United States Patent [19]

Delhaye et al.

[11] Patent Number: 4,589,292
[45] Date of Patent: May 20, 1986

[54] PROCESS AND APPARATUS FOR SAMPLING AMBIENT AIR AT A WORK PLACE

[76] Inventors: Jean-Noël Delhaye, 20 bis rue Roger Bouvry, 59113 Seclin (Nord); Elizabeth Kielczewska, 4, Allée des Charmettes, 59650 Villeneuve d'Ascq (Nord), both of France

[21] Appl. No.: 678,241

[22] Filed: Dec. 5, 1984

[51] Int. Cl.[4] .............................................. G01N 1/24
[52] U.S. Cl. ................. 73/863.03; 73/863.23; 73/864.34; 128/716
[58] Field of Search ........... 73/863.03, 863.23, 863.24, 73/863.25, 864.34, 864.35; 128/719, 730, 716, 721, 204.23, 204.22

[56] References Cited

U.S. PATENT DOCUMENTS

| | | | |
|---|---|---|---|
| 3,850,036 | 11/1974 | Sanctuary et al. | 73/863.03 X |
| 4,080,832 | 3/1978 | Moody et al. | 73/863.23 |
| 4,183,247 | 1/1980 | Allen et al. | 128/719 X |
| 4,202,212 | 5/1980 | Allen et al. | 128/719 X |
| 4,245,669 | 1/1981 | Schmidt | 73/863.23 |
| 4,246,788 | 1/1981 | Olin et al. | 73/863.03 |
| 4,254,657 | 3/1981 | Leichnitz et al. | 73/863.03 |
| 4,269,059 | 5/1981 | Baker | 73/863.03 |
| 4,389,903 | 6/1983 | Bertone et al. | 73/863.23 X |
| 4,432,248 | 2/1984 | Lalin | 73/863.03 |
| 4,452,252 | 6/1984 | Sackner | 128/721 X |

FOREIGN PATENT DOCUMENTS 40928 12/1981 European Pat. Off. ......... 73/864.35
733648 5/1980 U.S.S.R. ........................... 128/719

OTHER PUBLICATIONS

"A Personal Air Sampling Pump for Hospital Operating Staff"; *Journal of Medical Engineering and Technology;* vol. 2, No. 6, pp. 310-312; Nov. 1978; K. B. Carter et al.

*Primary Examiner*—Jerry W. Myracle
*Assistant Examiner*—Tom Noland
*Attorney, Agent, or Firm*—Robert E. Burns; Emmanuel J. Lobato; Bruce L. Adams

[57] ABSTRACT

A process for sampling ambient air at a work place comprises continually withdrawing by means of a pump, a sample of ambient air in the proximity of the respiratory tract of an individual worker, filtering the aspirated air for subsequent analysis of filtered-out particles, picking-up the cardiac rhythm of the individual and controlling the flow of air of the pump by a signal modulated by the cardiac rhythm of the individual. Apparatus for carrying out the process copmrises a sampling tube, a motor driven pump for drawing a sample of ambient air in through the sampling tube, a filter associated with the sampling tube for filtering the air sample, a photo electric device for picking up the cardiac rhythm of the individual and a control circuit for controlling the flow-rate of the pump by a signal modulated by the cardiac rhythm of the individul. The pump motor is further controlled by a pressure pick-up downstream of the filter to correct for flow attenuation by the filter.

7 Claims, 2 Drawing Figures

PROCESS AND APPARATUS FOR SAMPLING AMBIENT AIR AT A WORK PLACE

BACKGROUND OF THE INVENTION

The invention relates to a process for taking samples of air at a work place, and of a device for implementing this process. Its application will be found in the field for protecting persons exposed to atmospheric pollution.

The departments responsible for safety at work will control the degree of atmospheric pollution at work places, in industry in particular, by taking samples of the air breathed in by individuals at these work places where it is desired to check the level of pollution. At the present time, these samples are carried out by an independent pump worn by the individual at waist level and connected to a sampling tube which emerges near his respiratory tract.

This pump is equipped with a removable filter on which the dust and the particles present in the air breathed in by the individual are deposited. When the sampling is finished, the filter is withdrawn from the pump in order to carry out a quantitative and qualitative analysis of the products collected in the filter.

Now, it has not so far been possible to establish a correlation between the results of the blood analysis and those of the analysis of products collected on the filter of the sampling device. This absence of correlation is paradoxical, since it is in contradiction with numerous observations which have permitted the establishment, in an undeniable manner, that the composition of an individual's blood was a function of the atmosphere in which he breathed.

The sampling devices used at present work at a constant flow, and this means that they do not correctly simulate a person's breathing, since this depends closely on his physical activities. More precisely, the respiratory rhythm of an individual is correlated with his cardiac rhythm, both being functions of the physical effort made in positions which vary according to conditions.

SUMMARY OF THE INVENTION

The aim of the invention is to propose a process for sampling air which reproduces the respiratory rhythm of the individual for whom it is desired to check the surrounding atmosphere. In other terms, a process is proposed by which the volume of flows of air sampled are at any given moment proportional to the pulmonary output of the individual. For this purpose, the invention proposes that the working of the pump should be piloted by a signal dependent on the individual's cardiac rhythm.

The cardiac rhythmn could of course be picked up directly by means of electrodes on the chest of the person in question, as is current practice in establishing an electrocardiogram. However, the disposition of these electrodes is not really compatible with normal physical activity at the work place. Thus the invention proposes to pick up the cardiac rhythm from one of the ear lobes, using the properties of transparence of the lobe.

To reproduce more faithfully the respiratory rhythm of the individual, the process according to the invention also takes into consideration the phenomena of clogging which may be produced in the pump filter. For this purpose, the real flow of air at the filter will be compared with the theoretical flow of air obtained from the cardiac rhythm, and the necessary corrections will be made to maintain the desired flow at the pump.

The process for sampling the ambient air at a work place in which there is continuous aspiration of the ambient air in the proximity of the working individual's respiratory system by means of a pump, and the sampled air is filtered to analyse the particles present in the ambient air, is characterized by the fact that the cardiac rhythm of the individual is picked up, and the flow of the pump is piloted by a signal modulated by the cardiac rhythm.

The invention also proposes a sampling device applying this process. This device comprises in particular a tube for air sampling, an aspiration pump driven by a motor, connected to the sampling tube and fitted with a filter, and is characterized by the fact that it has means of calculating the respiratory rhythm from the measured cardiac frequency, and of piloting the motor of the pump so as to obtain a flow of air proportional to the pulmonary flow.

The invention will be better understood by reference to the description below and the drawing which is an integral part of it.

THE DRAWINGS

DESCRIPTION OF THE PREFERRED EMBODIMENTS

Figure 1:
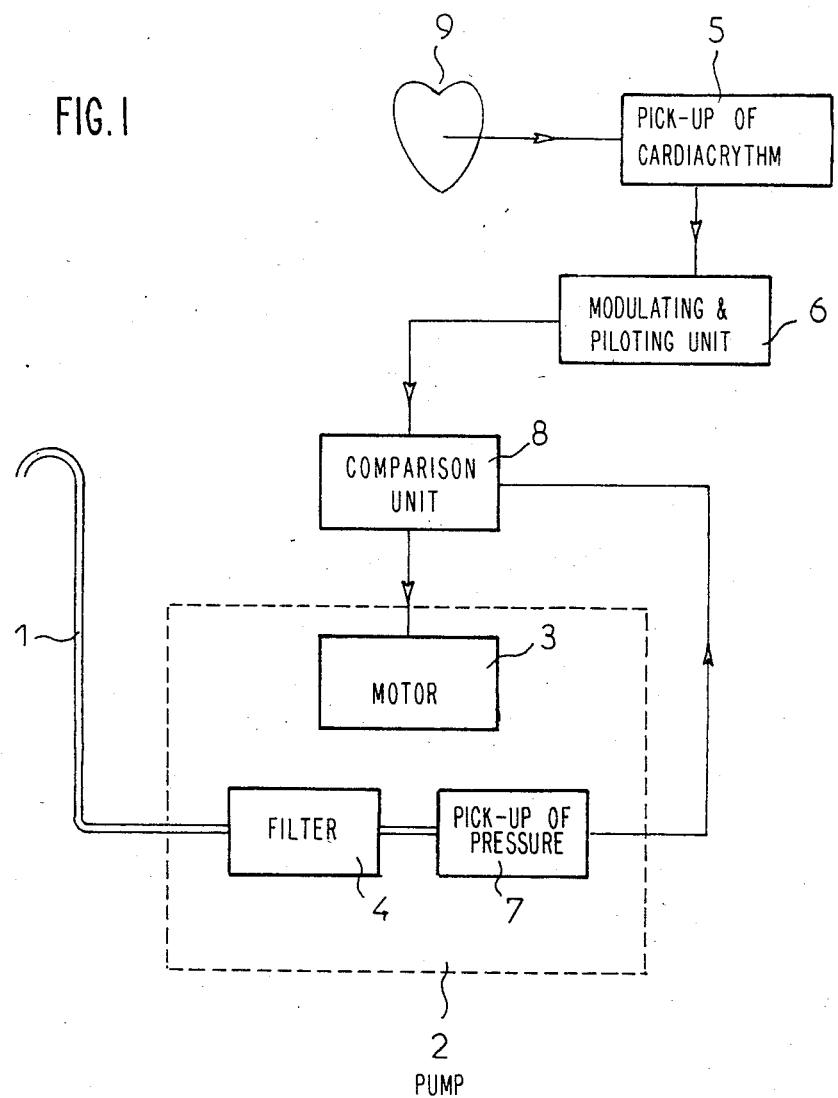
FIG. 1 illustrates diagramatically a method and device for sampling ambient air of a workplace.

The invention can be applied for any continuous sampling of the air breathed by an individual. This sampling can be carried out at a place of work, but it could equally well be carried out in any other place, for example, in an urban environment to control the level of pollution due to automobiles.

In the process according to the invention, there is a continuous aspiration of the ambient air in the proximity of the individual's respiratory tract by using an aspiration pump designed for this purpose, the characteristics of which can be easily determined by the specialist. This pump will be worn at waist level, and it will have an autonomous supply so as not to hamper the movements of the wearer.

The pump is also equipped with a filter in the form of a capsule in which the particles and dust present in the air aspired are collected.

The characteristic of the process according to the invention is to pilot the working of the aspiration pump with a signal obtained from the individual's cardiac rhythm. For this purpose, the cardiac rhythm is picked up so as to produce a signal reproducing the physical effort of the individual, and processing this signal so that it can pilot the motor driving the aspiration pump.

In this way, variations in cardiac frequency due to physical activity bring about (after numerical treatment) variations in the speed of the pump. This permits the accumulation on the filter of a quantity of dust proportional to that which has penetrated the human organism via the respiratory tract. The total volume of air aspired by the pump during the sampling and the volume of air in fact aspired by the individual can be read off on the displays.

However, to establish the relation between the cardiac and respiratory activities, it is necessary to take into account a coefficient which will be proper to each individual. This coefficient will be determined by the result of a test to which the individual will be subjected before the air samplings are carried out.

To take into account the phenomena of clogging due to the accumulation of dust on the filtering surface, the process according to the invention provides for the flow of air to be measured downstream from the filter, and for this flow to be compared with the theoretical flow determined according to the cardiac rhythm. If it appears that there is a difference between these two rates of flow, a correction will be made to the supply tension of the pump motor so as to eliminate this discrepancy. In consequence, if the cardiac rhythm reveals a constant respiratory rhythm, the sampling of air will also be carried out at a constant flow.

Furthermore, to make it easier to pick up information on the cardiac rhythm, this will be picked up directly from the lobe of one of the ears, using the transparence of the lobe under the action of a luminous flux which is periodically masked by the blood flux.

The single FIGURE illustrates a device implementing this process. This device comprises first of all a sampling tube 1, of a type which can be easily determined by a specialist. The upper extremity of this tube emerges close to the respiratory tract of the individual, and its lower extremity will be connected to a pump 2 fixed at the level of the wearer's waist. This pump 2 is driven by a motor 3, connected to a rotor, not represented, which creates a movement of aspiration of the air in the proximity of the upper opening of the air sampling tube 1. The air aspired passes through a filter 4, which has a filtering surface adapted to collect the fine dust and the various particles borne by the air aspired.

The device also comprises a pick-up for cardiac rhythm 5 which supplies a signal reproducing the cardiac rhythm. This pick-up could be placed in the direct proximity of the heart or, for reasons of convenience, in the proximity of a blood vessel.

The signal supplied by the pick-up 5 is transmitted to a modulation and piloting unit 6 which transforms a signal of variable frequency into a signal of variable tension applied directly to the terminals of the pump motor 3. The modulation unit should have a very short response time, seeing that the cardiac signal can attain a frequency of 180 hertz.

In a preferred mode of execution, the pump will be equipped with a pressure pick-up 7 which will allow the flow of air aspired downstream of the filter 4 to be determined. The information on this flow will be transmitted to a comparison unit 8 whose function will be to determine the discrepancy between the flow calculated by the modulation unit and that flow measured by the differential pressure pick-up 7. If the discrepancy calculated by the comparison unit is negative, this unit will transmit a signal to the pump so as to increase its speed and, conversely, if the comparison unit detects a positive discrepancy, it will transmit a signal to the motor to reduce the flow of aspired air.

Figure 2:
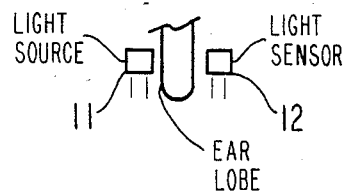
FIG. 2 illustrates schematically means for picking up the cardiac rhythm of an individual.

In a preferred mode of execution as illustrated in FIG. 2, the cardiac rhythm pick-up 5 will be located at the lobe of one of the ears, and it will comprise a device 11 allowing a luminous flux to be sent in the direction of the blood vessel transversing the lobe, and receiving means 12 on the opposite side of the ear lobe for measuring the luminous intensity transmitted through the zone masked by the blood vessel, if the source of the light is considered.

The source of luminous flux and the receiver can be of any desired type.

We claim:

1. Process for sampling ambient air at a work place which comprises continually withdrawing by means of a pump, a sample of ambient air in the proximity of the respiratory tract of an individual worker herein after referred to as "said individual", filtering the aspirated air sample with a view to subsequently analyzing the particles filtered out of the air sample and thereby determining particles present in the ambient air,
   picking up the cardiac rhythm of said individual, and
   controlling the flow of said pump by a signal modulated by the cardiac rhythm of said individual.

2. Process according to claim 1, in which the flow of air sampled is measured after it has been filtered, the flow thus measured is compared with the flow determined by the signal modulated by the cardiac rhythm of said individual and, if any discrepancy is detected between these two flows, the flow of the pump is controlled so as to eliminate such discrepancy.

3. Process according to claim 1, in which the modulated signal controlling the flow of said pump is modified by a coefficient determined by the relation of cardiac and respiratory activities of said individual.

4. Process according to claim 1 in which the cardiac rhythm of said individual is picked up by sensing the pulsed flow of blood in an ear lobe of said individual.

5. Apparatus for sampling ambient air at a work place which comprises,
   a sampling tube having an inlet positioned in the proximity of the respiratory tract of an individual worker hereafter referred to as "said individual",
   pump means connected with said sampling tube for continually drawing a sample of ambient air through said sampling tube,
   filter means associated with said sampling tube for filtering the air sample drawn in through said sampling tube and thereby filtering out for subsequent analysis particles present in the air sample,
   means for picking up the cardiac rhythm of said individual, and
   means for controlling the flow of said pump means by a signal modulated by the cardiac rhythm of said individual.

6. Apparatus according to claim 5, further comprising means for measuring the flow of air downstream of said filter means, and means for comparing the flow determined by said downstream measuring means with the flow determined by the signal modulated by said cardiac rhythm and for controlling said pump means to eliminate any discrepancy between the flow determined by said downstream measuring means and the flow determined by said signal modulated by said cardiac rhythm.

7. Apparatus according to claim 5, in which said means for picking up the cardiac rhythm of said individual comprises a light source for directing light through an ear lobe of said individual, and a sensor on the opposite side of said ear lobe for receiving light transmitted through said ear lobe modulated by flow of blood in said ear lobe.

* * * * *